US007381686B2

United States Patent
Lin et al.

(10) Patent No.: US 7,381,686 B2
(45) Date of Patent: Jun. 3, 2008

(54) COMPOSITE FOR INHIBITING ALGAE GROWTH AND USE THEROF

(75) Inventors: Shiue-Lian Lin, Taipei (TW); Shuo-Ting Hung, Taipei (TW); Lu-Pei Hu, Miaoli (TW); Po-Hsun Chang, Taipei (TW); Hong-Ming Lin, Sinjhuang (TW); Ching Chuan Lin, Taipei (TW)

(73) Assignees: Taikong Corp., Taipei (TW); Apex Nanotek Corporation, Taipei County (TW)

( * ) Notice: Subject to any disclaimer, the term of this patent is extended or adjusted under 35 U.S.C. 154(b) by 276 days.

(21) Appl. No.: 11/115,339

(22) Filed: Apr. 27, 2005

(65) Prior Publication Data

US 2006/0243675 A1    Nov. 2, 2006

(51) Int. Cl.
*C02F 1/50* (2006.01)
*A01N 59/16* (2006.01)

(52) U.S. Cl. ............... 504/152; 210/764; 210/501; 422/28; 424/618; 424/641

(58) Field of Classification Search ........... 504/152
See application file for complete search history.

(56) References Cited

U.S. PATENT DOCUMENTS

| 5,531,869 | A | * | 7/1996 | Kubo ...................... 502/202 |
| 5,824,267 | A | * | 10/1998 | Kawasumi et al. ........ 422/28 |
| 6,379,712 | B1 | * | 4/2002 | Yan et al. ................. 424/618 |
| 6,653,519 | B2 | * | 11/2003 | Koper et al. .............. 588/313 |
| 6,827,766 | B2 | * | 12/2004 | Carnes et al. ............ 106/15.05 |
| 6,962,714 | B2 | * | 11/2005 | Hei et al. ................. 424/405 |
| 6,994,794 | B2 | * | 2/2006 | Hansen et al. ............ 210/764 |

FOREIGN PATENT DOCUMENTS

JP      2001149946 A  *  6/2001
JP      2004065080 A  *  3/2004

OTHER PUBLICATIONS

Office Action of Chinese application counterpart 2005100806875, Aug. 20, 2007.

* cited by examiner

*Primary Examiner*—Peter A. Hruskoci
(74) *Attorney, Agent, or Firm*—WPAT, P.C.; Anthony King

(57) ABSTRACT

A composite for inhibiting algae growth comprising a polypore base carrier and a nano-metal mixture coated on the carrier, wherein the mixture comprising a nano-metal particle and a substance for fixing the particle on the carrier.

9 Claims, 1 Drawing Sheet

(A)

(B)

(C)

(A)

(B)

(C)

COMPOSITE FOR INHIBITING ALGAE GROWTH AND USE THEROF

FIELD OF THE INVENTION

The present invention relates to a composite for inhibiting algae growth. The invention also relates to a method for inhibiting algae by using the composite of the invention.

BACKGROUND OF THE INVENTION

In industry, aquaculture and domestic applications in which rely heavily on water supply, it's important to control the water quality at a desired condition.

Water containers used to haul and store water for human and animal consumption, water for household use, and water for agricultural chemical spraying. Such applications require relatively pure and uncontaminated water.

In one important aspect, algae growth in a small amount of water retained in the container over a significant period of time can be considerable, which is highly undesirable.

Algae induce many problems: clogging of filters in water filtration devices, exhaustion of dissolved oxygen, and suffocation of fishes and shellfishes to death.

Algae come in many forms. There are microscopic, one-celled algae, filamentous algae that resemble hair, algae that grow in sheets and macroalgae that look like plants. There are even algae that live inside the outer integument ("skin") or calcium shell of some corals, anemones, and other sessile invertebrates called zooxanthellae. There are slimy-looking algae that are often not algae at all, but a colony of primitive photosynthetic organisms known as cyanobacteria. There are also very hard-to-remove little dots of green that sometimes grow on aquarium panels which also are not algae, but diatom or radiolarian colonies (microscopic, one-celled, animals with hard shells) with algae incorporated in their matrix.

In an aquarium, algae growth is inevitable. Algae consume nutrients in the aquarium that if allowed to accumulate, are harmful to fish.

Algae control can be divided into three or four categories: In general on the basis of most to least appropriate in terms of long term cost, safety and ease of use these are biological, mechanical, physical and chemical controls. A few pertinent facts hold for all methods of algae control.

Turbo and Astrea snails, some blennies, some tangs, among others are good grazers. Snails are the most widely used scavengers, and generally the best choice. Some parts of the country seem to favor the use of sea urchins, dwarf angels. The former die too easily and move the decor about, and the latter can be problematical with eating expensive invertebrates.

State of the art methods include functional protein skimmers, with or without ozone and ultraviolet sterilizers. These physical filters remove and destroy algae on exposure and help oxidize nutrients as the water is circulated.

Using any chemical to control algae is the least desirable route in terms of safety and long term effect. There are several brands of antibiotic (Erythromycin, or equivalent generic name) on the market; all should be avoided from different viewpoints. The problem being they treat the symptoms only without dealing with the cause(s) of the algae problem. The factors can contribute to water system being out of balance. There are the obvious downsides of altering the chemical "evolution" of water system as well. Leave us not forget anti-biotic means "against life".

In commercial and public aquaria settings copper, usually in some format of copper sulfate solution is employed as an algicide, as well as a general epizootic parasite preventative. If you have or ever intend to keep invertebrates, macro-algae, live rock in the system do not get involved in using copper. This metal is superb in treatment and quarantine tanks, dips and fish-only arrangements. The trade uses it extensively; but it is persistent and toxic to all life, especially non-fish.

If using a chemical algicide, great care on the dosage must be taken and be on the lookout for below acute toxic side effects. Several products state that under "bad conditions" the dosage may be doubled or tripled. It causes inconvenient to practice in algae control.

Most algaecidal agents available in market are formulated as liquids; however, such liquid formulations have certain disadvantages, notwithstanding their overall effectiveness in eradicating algae. For example, liquid algaecidal agents comprising sodium hypochlorite have limited shelf lives, generally ranging from six to eight months. Transportation of liquid formulations can also be expensive and hazardous if large quantities of the algaecidal composition are desired (generally, a gallon solution comprises about 10% of sodium hypochlorite). A concentrated algaecidal solid formulation can be more easily shipped.

SUMMARY OF THE INVENTION

Figure 1:
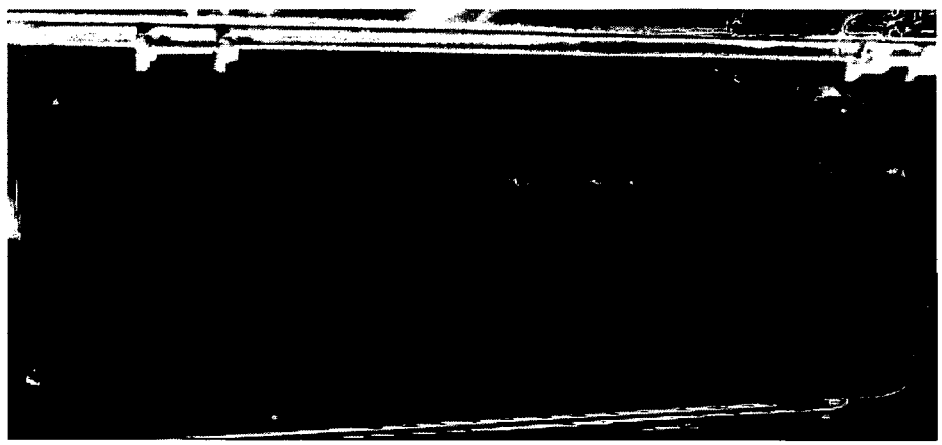
FIG. 1 illustrates the effect of inhibiting algae growth by the use of the composite of the invention.
Figure 1:
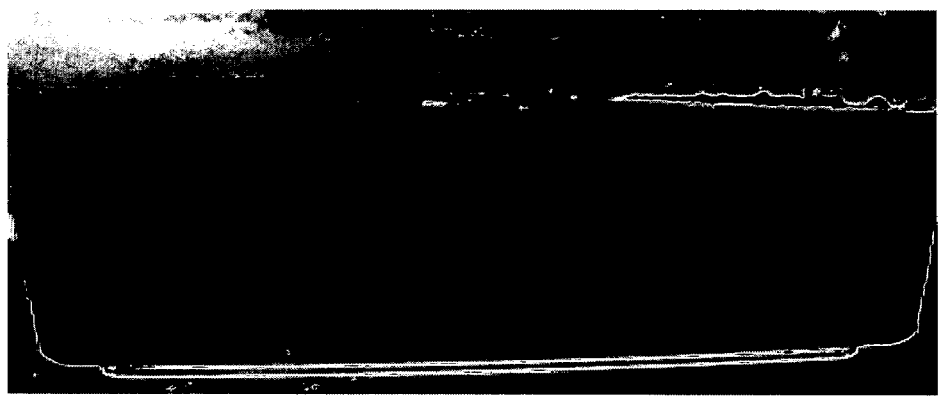
Figure 1:
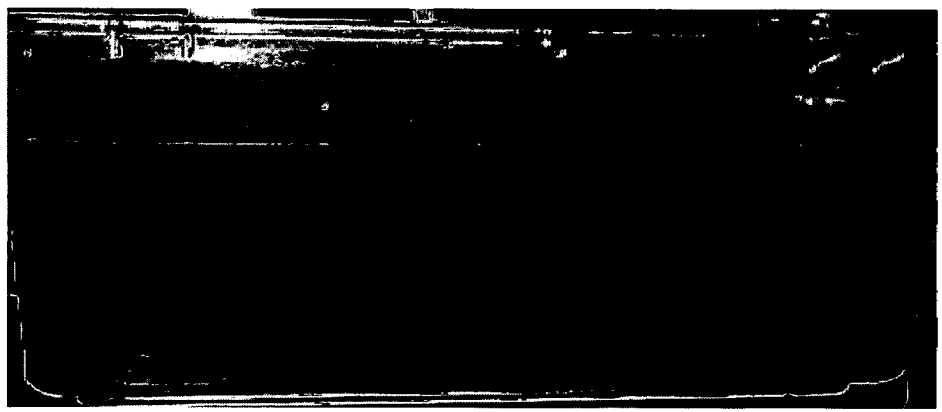

The present invention relates to a composite for inhibiting algae growth comprising a polypore base carrier and a nano-metal mixture coated on the carrier, wherein the mixture comprising a nano-metal particle and a substance for fixing the particle on the carrier.

The present invention further relates to a method for inhibiting algae comprising applying the composite of the invention to the place containing algae.

DETAILED DESCRIPTION OF THE INVENTION

The present invention provides a composite for inhibiting algae growth comprising a polypore base carrier and a nano-metal mixture coated on the carrier, wherein the mixture comprising a nano-metal particle and a substance for fixing the particle on the carrier.

In the composite of the present invention, the base carrier could be any suitable carrier carrying nano-metal mixture of the invention. For example, clay, ceramic, oxidized metal, plastic, and polymer could be applied to the invention. In the preferred embodiment, the base carrier is polypore base carrier. In the more preferred embodiment, the base carrier is ceramics. In the most preferred embodiment, the base carrier is in a form of ceramics chondrite water filter.

Nanosilver

Silver has long been known to inhibit the oxygen-exchange in bacteria, killing the bacteria. Nanosilver directly gets inside the bacteria and combines with oxygenic metabolic enzymes (—SH) to suffocate bacteria. As a result, it is capable of killing most microbes that it contacts, including bacteria, epiphytes, moulds and spores. Nanosilver has overall antibiotic activity on such drug-resistant pathogenic bacteria as drug-resistant *colibacillus*, drug-resistant *staphylococcus aureus*, drug-resistant *pseudomonas aeruginosa, pyococcus*, drug-resistant enteric *bacilli* and anaerobes; can sterilize such bacteria affixed on scalds and traumas as *staphylococcus aureus, colibacillus, pseudomonas aeruginosa, candida albicans* and other G+, G− pathogenic bacteria; and can substantially kill gonococcus that propagates venereal diseases.

The nanosilver particle used in the composite of the invention has a crystal particle size from 10 to 100 nm in diameter.

Substance

In the composite of the present invention, the substance for fixing the particle on the carrier is any material suitable to fix the nano-metal particles on the base carrier. Preferably, the substance is nano-zinc oxide in needle, dendrite or wire shape. In the most preferred embodiment, the substance is nano-zinc oxide in a uniform tetrapod shape such as Zinc Oxide Whisker (ZnOw).

Zinc Oxide Whisker (ZnOw), has a tetrapod shape in micro-image and porous appearance in bulk. ZnOw possess good comprehensive properties such as high strength, semi-conductivity, wear-proof, vibration insulation, microwave absorption and antibacterial effect. It can be widely used as functional and structural material, which is dominant for its peculiar shape along with the single crystalline character.

Like photocatalyst, the nano-zinc oxide has cracking ability on debris of pathogens (such as bacteria) to purify water quality.

Tourmaline

The composite of the present invention further comprises tourmaline. The tourmaline is selected from the group consisting of black (schorl), brown (dravite), blue (indicolite), pink (rubellite), green, yellow, orange, multicolor and clear tourmaline.

Tourmaline is one kind of natural mineral. It belongs to siliceous rock mineral with multiple elements. Its chemical components are mainly silicate, boron, magnesium, aluminum and trace elements beneficial to human body, such as magnesium, iron, and cesium, etc. Its chemical general formula is $NaR_3Al_6[Si_6O_{18}][BO_3]_3(OH,F)4$. Its crystal belongs to the general name of a group of circular structure silicate mineral in three-dimension crystal system. In the formula, the letter R represents positive ion of metal. The kinds and contents of R directly influence the color of tourmaline. When R is $Mg^{2+}$, $Fe^{3+}$, or $(Li^++Al^{3+})$, it respectively composes magnesium tourmaline, black tourmaline and lithium tourmaline three end member.

Tourmaline is mostly relative with pneumatolysis. Generally its provenance is granite pegmatite and metamorphic rock formed by metasomatism. The crystal with piezoelectricity can be used in wireless industry. The crystal with bright color and luster can be made into gem that is called jade royal seal in China. When tourmaline is heated, two ends of crystal will bend or distortion and induce the positive-negative static. This kind of mineral is called "Electric Stone" just due to its thermoelectric property. Its English name is "Tourmaline" derived from the word of ancient Singhalese "Turmali" that means "mixed gem".

The color of tourmaline is different when its component is different. With abundant iron it is black. With abundant lithium, manganese or cesium it is rosiness or navy blue, respectively. With abundant magnesium, it shows brown or yellow color. With chrome, it is bottle green.

According to its shape, tourmalines have crystal tourmaline, fiber tourmaline and craftwork tourmaline. From its color and special optical effect, it can be divided into red tourmaline (also called "red jade royal seal"), green tourmaline (also called "green jade royal seal"), yellow tourmaline (also called "yellow jade royal seal"), purple tourmaline (also called "purple jade royal seal"), colorless tourmaline (also called "colorless jade"), black tourmaline (also called "black jade royal seal"), multiple color tourmaline (also called "multiple color jade royal seal" or "mottle jade royal seal") and tourmaline opal, etc.

Tourmaline will active and reduce molecule group of water and increase natural mineral materials through physical action, such as anioning, FIR (far infrared ray) and electrolysis of water. It activated the purification, and mineralization of water that benefited to human body. The features can be described as the following:

A、Generating Negative Ion

The negative ion is also named as "vitamin of air". It can regulate the ion balance of human body. It has the function of activating cell, increasing natural cure capability and inhibiting oxidation or aging. It also removes odor.

B、Electrolyzing Water

After water is electrolyzed, it can obtain various effects, such as interface active action, chloric stabilization, ferric passivation (prevent iron oxidation and occur red water), water deoxidization, removing silicon dioxide and bindings (microbe aggregates), etc. When tourmaline reacts with water, it is able to settle problems that chemical lotion and chemical substance is hard to resolve.

C、Reducing Molecule Group of Water

Water molecule ($H_2O$) is not existed by oneself. Its molecule would combine with each other and form molecule bundle. The molecule bundle can remove or filter impurities and enhance body infiltration.

D、Radiating FIR (Far Infrared Ray) (4-14 Micronmeter Ray)

Increase the numbers of dissolved oxygen in the water. Promote blood circulation and accelerate metabolism. Benefit to human body absorption. Regulate and balance pH of water to enhance resistibility.

E、Containing Effective Minim Mineral Substance

Water passed through it can separate out certain mineral substance and microelement benefited to human body, such as zinc, calcium, magnesium, potassium and strontium, etc. It is easy to be absorbed by human body and is the best mineral source.

In the preferred embodiment, the tourmaline is pink tourmaline.

Concentration

In the nano-metal mixture coated on the carrier, the components in the mixture comprise 1000 to 3500 ppm of nanosilver and 500 to 2000 ppm of zinc oxide based on the total quantity of the carrier. The concentration of nanosilver is preferably 1000-2500 ppm, more preferably 1000-2000 ppm, and most preferably 2000 ppm. The concentration of zinc oxide is preferably 500-2000 ppm, more preferably 1000-2000 ppm, and most preferably 1500 ppm.

In the preferred embodiment, the mixture further comprises 100 to 1000 ppm of tourmaline based on the total quantity of the carrier. The concentration of tourmaline is preferably 150-500 ppm, more preferably 150-300 ppm, and most preferably 250 ppm.

In practice, the composite of the invention is sufficient to convert the water from green to colorless in appearance.

The present invention further relates to a method for inhibiting algae comprising applying the composite of the present invention to the place containing algae.

The place is a container with water, such as aquarium, swimming pool. In the preferred embodiment, the aquarium include animal (such as fish).

In the method of the invention, the concentration of nanosilver released by the coated polypore consumable substance is sufficient to convert the water from green to colorless in appearance.

The following examples are not intended to limit the scope of the invention, but are intended to illustrate the various aspects of the invention.

EXAMPLES

Example 1

Preparation of Ceramics Chondrite Coating of Nanosilver-zinc Oxide Whisker-Pink Tourmaline Mixture Procedure I:

Preparation of Base Carrier—Polyporous Ceramics Chondrite

1. Material

Materials: clay; nano-$Al_2O_3$; nano-$ZrO_2$; nano-$SiO_2$ and nano-SiC.

Control factors: purity, density, chemical to compose, powder size, a hole broken, wear and tear, absorbability, shape and quantity.

2. Molding

To pour thick liquid to shape up; slip casting, press to exit, scraping cutter, tape casting; and injection molding.

Control factors: removal of organic substance (such as binder).

3. Sintering

Hot shutter, rapid to burn reaction, hot-isostatic-pressing

Control factors: sintering thermometric; a curve control and shrink rate

4. Processing

Nanosilver spreading and separating control.

Procedure II:

Preparation of Nanosilver-Zinc Oxide Whisker (ZnOw)-Pink Tourmaline Mixture:

A homogeneous mixture in pure water was prepared according the following formula:

Components:

| | | |
|---|---|---|
| (a) Nanosilver | 2000 ppm |
| (b) ZnO Whisker | 1500 ppm |
| (c) Pink Tourmaline | 250 ppm |

At room temperature 25° C., the components (a), (b) and (c) were added to pure water and mixed the mixture. Then, the mixture was maintained 3 to 5 hours to produce the homogeneous mixture readily for use in the next step.

Procedure III

Ceramics Chondrite Coating of Nanosilver-Zinc Oxide Whisker-Pink Tourmaline Mixture The coating process of nanosilver-ZnOw-pink tourmaline mixture is listed below:

a. immersing ceramic particle in nanosilver-ZnOw-pink tourmaline mixture prepared in process II completely without disturbance for 1 hour, b. retrieving the ceramic particle from the mixture, c. heat treating the ceramic particle at temperature from 80-120° C. in a nitrogen atmosphere for 15-30 minutes, and d. baking the particle dry by natural heat dissipation under 500° C.

Example 2

Property Analysis of Ceramics Chondrite

The properties of the ceramics chondrite samples are set forth below in Tables 1 and 2.

TABLE 1

Chemical analysis data of the ceramics chondrite

| Composition | $SiO_2$ | $Al_2O_3$ | ZnO | $ZrO_2$ | MgO | others |
|---|---|---|---|---|---|---|
| Wt % | 19.34 | 61.12 | 7.84 | 3.26 | 6.40 | 2.04 |

TABLE 2

Physical analysis data of the ceramics chondrite

| Appearance | Dark red and white, polyporous 4~8 mm |
|---|---|
| Density | 2.56 g/cm$^3$ |
| Rate of hole | 35% |
| Rate of broken and tear | 1.03% |
| Rate of hydrochloric acid solubility | 2.53% |
| Absorption | same as active carbon |

Example 3

Bactericidal Effect of Ceramics Chondrite Water Filter

The ability of microorganism inhibition of ceramic chondrite was demonstrated.

The antimicrobial properties of the ceramic chondrite were evaluated by ASTM E2149-01 (American Society for Testing and Materials, 2001), which is a quantitative antimicrobial test method performed under dynamic contact conditions. *E. coli* (ATCC 11229) was used as a test organism. The incubated test culture in a nutrient broth was diluted with a sterilized 0.3 mM phosphate buffer (pH 7.2) to give a final concentration of $10^5$~$10^6$ colony forming unit (CFU/ml). This solution was used as a working bacterial dilution.

Each ceramic chondrite (1.08 g, nanosilver treated and untreated i.e. Control group) was first subjected to UV light sterilization, then transferred to a 10 ml test tube containing 3 ml of the working bacterial dilution, allowing a sufficient exposure of test subjects.

All tubes were capped loosely, placed on the incubator, and shaken at 37□ and 120 rpm using an incubator shaker (New Brunswick Scientific, N.J., USA). The tubes were shaken for 1 min±5 sec. Each tube was considered to a "0" contact time. To a 1.5 ml tube, 0.2 ml±0.002 ml of mixture from each test tube was immediately transferred, serially diluted and plated out. After transferring, the tubes was capped and placed on a wrist-action shaker for 3 hr and 6 hr. Bacterial concentration of each sample (3 hr and 6 hr) was identified by performing serial dilutions according to plate out techniques under "0" contact time. The inoculated plates were incubated at 37□ for 18 hours. The average values of the duplicates were converted to CFU/ml in the tubes by multiplying by the dilution factor.

The antimicrobial activity was expressed in terms of percent reduction of the organism after contact with the test specimen using the following equation, Reduction, % (CFU/ml)=(B−A/B)×100%; where A and B are the surviving cells (CFU/ml) for the tubes containing test samples (NMA-HTCC treated cotton) after the specified contact time (3 hr or 6 hr) and "0" contact time, respectively. The test results were stated in Tables 3 and 4.

TABLE 3

| Test group | Cell number of "0" contact time (CFU/ml) | Cell number of 3 hour contact time (CFU/ml) | Reduction (%) |
|---|---|---|---|
| Control group | $8.15 \times 10^5$ | $1.06 \times 10^8$ | — |
| Nanosilver group | $8.9 \times 10^5$ | <10 | >99.99 |

**The inoculated plates were incubated at 37□ for 3 hours, independent tests and surviving cells were counted.

TABLE 4

| Test group | Cell number of "0" contact time (CFU/ml) | Cell number after 6 hour contact time (CFU/ml) | Reduction (%) |
|---|---|---|---|
| Control group | $8.15 \times 10^5$ | $6.9 \times 10^9$ | — |
| Nanosilver group | $8.9 \times 10^5$ | <10 | >99.99 |

**The inoculated plates were incubated at 37□ for 6 hours, independent tests and surviving cells were counted.

In the present example, the ceramic chondrite, with nanosilver treated showed superior antimicrobial effect, wherein a percent reduction of 99.99% was observed.

Example 4

Effect of Inhibiting Algae Growth by using the Composite of the Invention

The ceramics chondrite coating of nanosilver-zinc oxide whisker-pink tourmaline mixture prepared by Example 1 was applied to 2 liter tank (FIG. 1(A)) to test the inhibition of algae.

After applying 6 grams of the ceramics condrite in a 2 liter tank, it clearly showed that the green color significantly reduced after 24 hours (FIG. 1(B)). As shown in FIG. 1(C), it is surprising that the color was almost clear after applying 48 hours of the ceramics condrite of the invention while the fish in the tank survived very well.

What is claimed is:

1. A composite for inhibiting algae growth in water comprising a polypore base carrier and a nano-metal mixture coated on the carrier, wherein the mixture comprising a nano-silver particle and a nano-zinc oxide for fixing the particle on the carrier, and tourmaline, wherein said composite is sufficient to inhibit said algae growth, and convert the water from green to colorless in appearance.

2. The composite according to claim 1, wherein the base carrier is ceramics.

3. The composite of claim 1, wherein the substance is nano-zinc oxide in needle, dendrite or wire shape.

4. The composite of claim 1, wherein the nano-zinc oxide has cracking ability.

5. The composite of claim 1, wherein the tourmaline is selected from the group consisting of black (schorl), brown (dravite), blue (indicolite), pink (rubellite), green, yellow, orange, multicolor and clear tourmaline.

6. The composite of claim 5, wherein the tourmaline is pink tourmaline.

7. The composite of claim 1 wherein the mixture comprises 1000 to 3500 ppm of nanosilver and 500 to 2500 ppm of zinc oxide based on the total quantity of the carrier.

8. The composite of claim 7, wherein the mixture further comprising 100 to 1000 ppm of tourmaline based on the total quantity of the carrier.

9. The composite of claim 1, wherein the nano-silver particle has a crystal particle size from 10 to 100 nm in diameter.

* * * * *